(12) United States Patent
Sugahara et al.

(10) Patent No.: US 9,079,025 B2
(45) Date of Patent: Jul. 14, 2015

(54) GANTRY-TYPE PARTICLE BEAM IRRADIATION SYSTEM AND PARTICLE BEAM THERAPY SYSTEM COMPRISING SAME

(75) Inventors: Kengo Sugahara, Chiyoda-ku (JP);
Kazushi Hanakawa, Chiyoda-ku (JP);
Taizo Honda, Chiyoda-ku (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/380,784

(22) PCT Filed: Apr. 19, 2012

(86) PCT No.: PCT/JP2012/060570
§ 371 (c)(1),
(2), (4) Date: Aug. 25, 2014

(87) PCT Pub. No.: WO2013/157116
PCT Pub. Date: Oct. 24, 2013

(65) Prior Publication Data
US 2015/0031934 A1    Jan. 29, 2015

(51) Int. Cl.
*A61N 5/10* (2006.01)
*G21K 5/04* (2006.01)
*G21K 1/10* (2006.01)

(52) U.S. Cl.
CPC ............ *A61N 5/1042* (2013.01); *A61N 5/1048* (2013.01); *A61N 5/1077* (2013.01); *A61N 5/1081* (2013.01); *G21K 1/10* (2013.01); *G21K 5/04* (2013.01); *A61N 2005/1087* (2013.01); *A61N 2005/1095* (2013.01)

(58) Field of Classification Search
USPC ....................................... 250/492.3
See application file for complete search history.

(56) References Cited

U.S. PATENT DOCUMENTS

2004/0200983 A1* 10/2004 Fujimaki et al. ........... 250/492.3
2009/0283702 A1* 11/2009 Umezawa et al. ......... 250/492.3
2010/0288946 A1   11/2010 Honda et al.
(Continued)

FOREIGN PATENT DOCUMENTS

JP    2005-37214 A    2/2005
JP    2006-351339 A   12/2006
(Continued)

OTHER PUBLICATIONS

International Search Report (PCT/ISA/210) mailed on May 29, 2012, by the Japanese Patent Office as the International Searching Authority for International Application No. PCT/JP2012/060570.

*Primary Examiner* — Kiet T Nguyen
(74) *Attorney, Agent, or Firm* — Buchanan Ingersoll & Rooney PC (57) ABSTRACT

In gantry type particle beam irradiation system comprising a gantry and being configured to irradiate a particle beam, which has small emittance in X direction and large emittance in Y direction at an extraction position of a circular accelerator, from an irradiation nozzle installed in the gantry to an irradiation target, the irradiation nozzle has a ridge filter which is installed so as for a direction in which emittance in X direction is maintained to tilt to a direction which is perpendicular to a ridge of the ridge filter by a predetermined angle in the state where the gantry is a reference angle.

6 Claims, 10 Drawing Sheets

(56) References Cited

U.S. PATENT DOCUMENTS

2011/0012028 A1 1/2011 Harada et al.
2012/0228521 A1* 9/2012 Honda et al. ............... 250/492.3

FOREIGN PATENT DOCUMENTS

| WO | WO 2009/139037 A1 | 11/2009 |
| WO | WO 2009/139043 A1 | 11/2009 |

* cited by examiner

GANTRY-TYPE PARTICLE BEAM IRRADIATION SYSTEM AND PARTICLE BEAM THERAPY SYSTEM COMPRISING SAME

TECHNICAL FIELD

This invention relates to particle beam therapy system in which a particle beam is applied such as performing cancer treatment by irradiating a particle beam.

BACKGROUND ART

A particle beam therapy system has the configuration in which high-energy charged particles which are accelerated by an accelerator such as synchrotron are extracted as a particle beam from an accelerator and the particle beam which is extracted is transported to an irradiation chamber by particle beam transport system comprising vacuum ducts and deflection electromagnets and then the beam is irradiated onto an affected part of a patient.

Relative dose of a particle beam such as proton, carbon ion beam, etc. reaches a peak value at a deep portion from the surface of body, at a position where these particles stop, that is, just prior to a range of the particle beam. The peak value is referred to as Bragg Peak.

According to a method for treating a cancer by particle beam, the Bragg Peak is irradiated onto a tumor which is formed on human's internal organs. In addition to treatment of cancer, the above-mentioned method can be applied to a case in which a deep portion in body is treated. A part to be treated including a tumor is generally referred to as an irradiation target. A position of Bragg Peak (BP) is determined by energy of a particle beam to be irradiated, and the higher energy of a particle beam is, the deeper a position of Bragg Peak (BP) is formed. In performing particle beam therapy, it is necessary to form uniform dose distribution of particle beam in whole of an irradiation target, therefore, in order to give the Bragg Peak (BP) to whole area of an irradiation target; "spread of irradiation volume" of a particle beam is performed.

Figure 12:
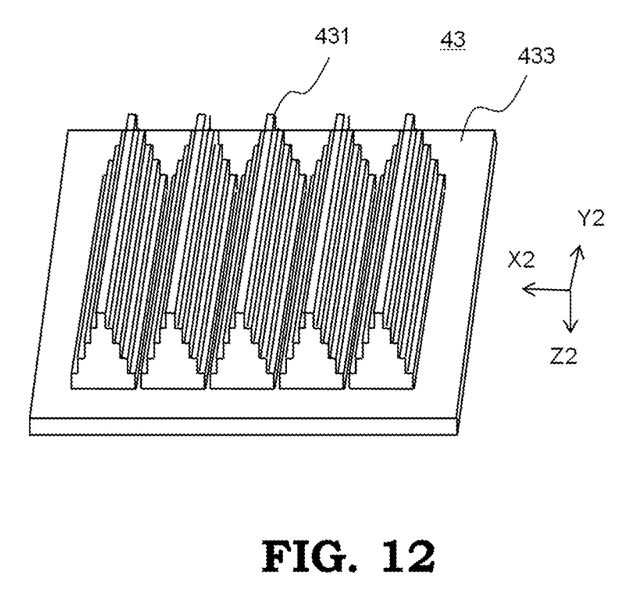
FIG. 12 is an oblique view showing a general ridge filter.

A device which is referred to as a ridge filter is used as a device to perform spread of irradiation volume in a depth direction (for example, Patent Document 1). A ridge filter is a device for spreading a width of energy of a particle beam. FIG. 12 is a perspective view showing the configuration of a ridge filter, and the ridge filter is a structure comprising triangular prisms having step-wise sides and the triangular prisms are arranged. This structure is manufactured by shaving a rectangular aluminum material so as to form its outside to be step-wise. Structures comprising triangular prisms are arranged so as for a particle beam to pass through in the direction of axis indicated by Z2 in FIG. 12. Energy of a particle beam is absorbed based on the travelling distance of a particle beam. Consequently, by varying a height from the lowest surface of structure of each step, energy after a particle beam passes through a ridge filter can be changed. Further, by changing a width of a step, a number of particles which passes through a part having a predetermined width of the structure can be changed.

After a particle beam which passes through a ridge filter, as a whole, energy width of the particle is spread. By irradiating an affected part with a particle beam whose energy width is spread, Bragg Peak (BP) having a width in a depth direction is formed, therefore an affected part which has a width in a depth direction can be irradiated with a particle beam.

On the other hand, due to fundamental restrictions of slow emission method, a particle beam which is extracted from a circular accelerator such as a synchrotron accelerator has the property which is different depending on a direction in a plane which is perpendicular to a travelling direction of a particle beam, that is, asymmetry property. When a travelling direction of a particle beam is Z-direction, a direction which is perpendicular to Z-direction and is of a beam circular track plane of an accelerator is X-direction, and a direction which is perpendicular to Z-direction and X-direction is Y-direction, a particle beam which is extracted has comparatively small emittance in X-direction and comparatively large emittance in Y-direction. This asymmetry property of emittance is particularly-problematic for a gantry type particle beam irradiation system which has the configuration such that an affected part is irradiated by changing an irradiation direction. Therefore, there is an example in which symmetrization of emittance is performed by arranging a scatterer in a particle beam transportation system. (For example, Patent Document 2). Further, there is so-called a corkscrew type of gantry which has the configuration such that a beam line is twisted in order to miniaturize whole of system (For example, Patent Document 3).

PRIOR ART REFERENCE

Patent Document

[Patent Document 1]
 International Publication WO2009/139037
[Patent Document 2]
 Japanese Patent Application Laid-Open No. 2006-351339
[Patent Document 3]
 U.S. Pat. No. 4,917,344

DISCLOSURE OF THE INVENTION

Problems to be Solved by the Invention

According to Patent Document 2, by arranging a scatterer in a particle beam transportation system, symmetrization of emittance can be realized. However, a scatterer is necessary, and there is a problem such that energy of particle beam is decreased, or utilization efficiency of a beam is decreased by a scatterer. On the other hand, a ridge filter has the asymmetric shape in an axial direction of a triangular prism, that is, a direction of a ridge, and in a direction which is perpendicular to the ridge. When a particle beam is passed through a ridge filter without symmetrization of emittance, depending on direction relationship between the direction of asymmetric of emittance and the direction of asymmetric of a ridge filter, asymmetry is exhibited in the effect of a ridge filter.

This invention aims to obtain a particle beam irradiation system which can realize spread of energy width in which change caused by an angle of gantry is small without decreasing energy of a particle beam, without decreasing utilization efficiency of a beam, in a case where a particle beam having emittance with asymmetric is irradiated on to an irradiation target by gantry type particle beam irradiation system in which a ridge filter is installed.

According to this invention, a gantry type particle beam irradiation system comprises a gantry and is configured to extract a particle beam from a circular accelerator, in a case where a direction in a circular track plane in the circular accelerator is defined as X direction in a plane which is perpendicular to a travelling direction of the particle beam at an extraction position of the circular accelerator, and the direction which is perpendicular to X direction in a plane which is perpendicular to the travelling direction of the particle beam is defined as Y direction, the particle beam has small emittance in X direction and large emittance in Y direction, and the particle beam which is transported by a particle beam transportation unit is irradiated from the irradiation nozzle to an irradiation target, wherein the irradiation nozzle has a ridge filter, in a position where the particle beam is incident on the irradiation nozzle, an angle of the gantry, by which the particle beam is transported so as for emittance in X direction and emittance in Y direction at the extraction position of the circular accelerator to be separated and to maintain each emittance is defined as a reference angle, in the state where the gantry is the reference angle, the ridge filter is installed so as for the direction in which emittance in X direction is maintained is tilted to the direction which is perpendicular to a ridge of the ridge filter by a predetermined angle.

Advantage of the Invention

A gantry type particle beam irradiation system which can realize spread of energy width having change which slightly depends on an angle of gantry can be obtained.

EMBODIMENT 1

Figure 1:
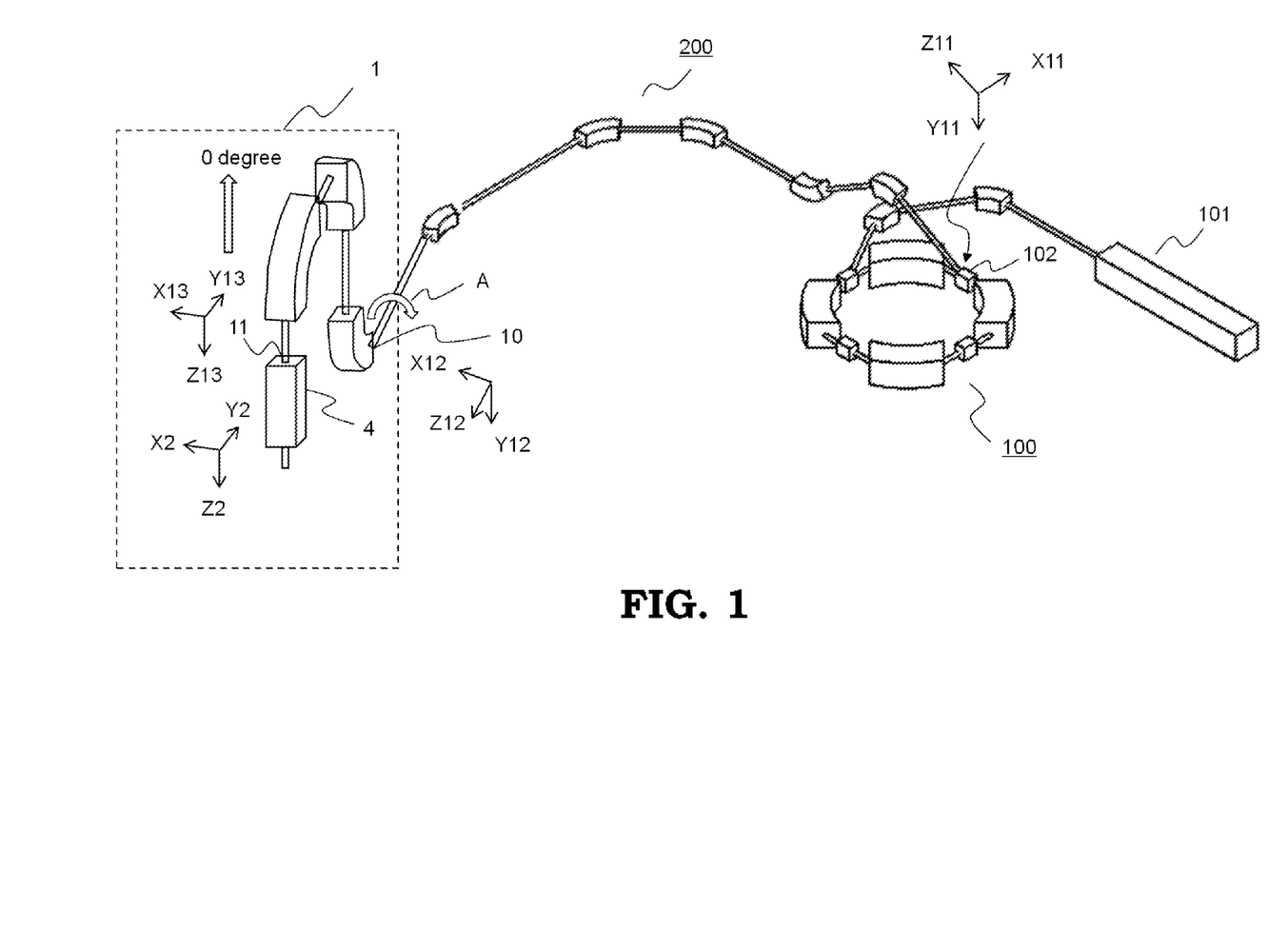
FIG. 1 is a diagram showing an outline of configuration for describing a particle beam irradiation system which is installed in a particle beam therapy system in Embodiment 1 of this invention.
Figure 2:
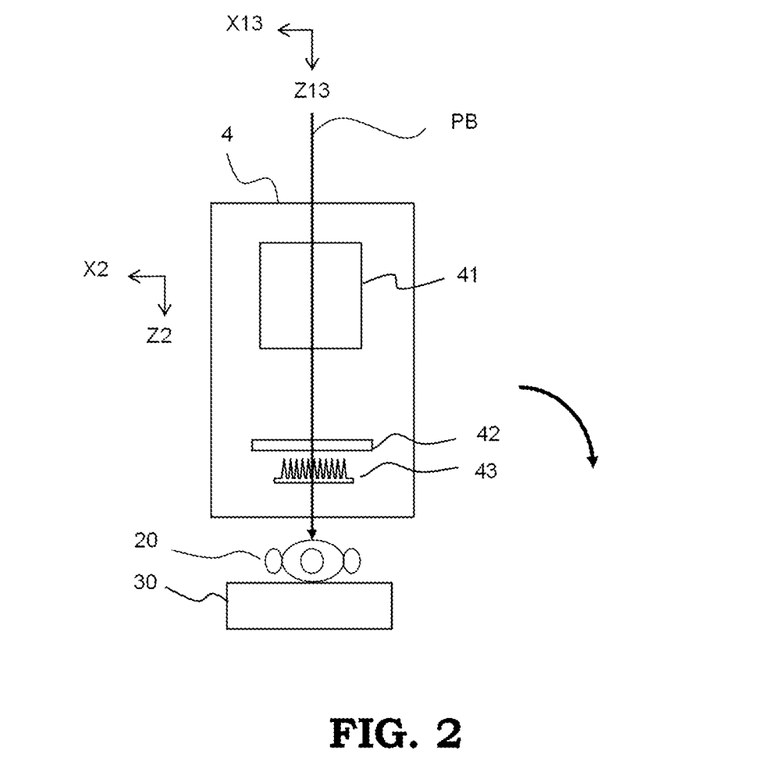
FIG. 2 is a cross section showing an outline of configuration of an irradiation nozzle of a particle beam therapy system in Embodiment 1 of this invention.

FIG. 1 is a diagram showing an outline of configuration for describing a particle beam irradiation system which is installed in a particle beam therapy system in Embodiment 1 of this invention. FIG. 2 is a cross side section showing an outline of configuration of an irradiation nozzle of a particle beam irradiation system in Embodiment 1 of this invention. A charged particle beam such as proton or carbon which is incident on a synchrotron accelerator 100 from an ion source 101 is accelerated in the synchrotron accelerator 100 comprising electromagnets, an acceleration cavity, vacuum ducts, etc. in a ring-state. The accelerated charged particles are extracted from an extractor 102 as a particle beam to the outside of the synchrotron accelerator 100. The particle beam which is extracted is transported in a particle beam transportation unit 200 comprising vacuum ducts, electromagnets, etc. and is incident on a gantry type particle beam irradiation system 1.

General gantry-type particle beam irradiation system 1 (may be simply referred to as "gantry 1") comprises deflection electromagnets for deflecting a particle beam twice or three times, and is configured so as to irradiate a particle beam from an irradiation nozzle 4 to an irradiation target. As indicated by arrow A, the gantry-type particle beam irradiation system 1 is configured so as to rotate around a travelling axis of a particle beam which is incident, that is, an axis in the direction indicated by Z12 in FIG. 1.

The irradiation nozzle 4 is configured as shown in an outline drawing FIG. 2. FIG. 2 is a cross section when an angle of the gantry 1 is an angle shown in FIG. 1, and the irradiation nozzle 4 is viewed from the direction of Y2 axis. A particle beam PB which is incident on the irradiation nozzle 4 is deflected to the direction which is perpendicular to a travelling direction of a particle beam by a scanning electromagnet 41 and is moved so as to irradiate an affected part, which is an irradiation target, of a patient 20 who lies down on a treatment table 30. In the downstream of the scanning electromagnet 41, a dose monitor 42 for monitoring irradiation dose and a ridge filter 43 as equipment for spreading energy width are arranged. As the irradiation nozzle 4 is installed in the gantry 1, the irradiation nozzle 4 is configured to rotate around the patient 20 as indicated by curve line with arrow, and a particle beam can be irradiated onto the patient 20 from various directions.

Here, the details regarding a direction of a particle beam which is closely-linked to this invention will be described. A particle beam is extracted from the extractor 102 of the synchrotron accelerator 100 to the outside of the synchrotron accelerator 100. In the synchrotron accelerator 100, a charged particle circulates in a track which is formed of electromagnets and is accelerated every time the charged particle passes through an acceleration cavity. A plane containing center of the track which is formed by circulating the charged particle is called as a circular track plane of an accelerator. As the synchrotron accelerator 100 generally has a large track whose diameter is several tens meters (an accelerator for medical use is small-sized and has a diameter of 10 m to 20 m), the circular track plane is horizontal plane generally. A beam axis of a charged particle beam which is extracted from the synchrotron accelerator 100 is as a particle beam is contained in a circular track plane. As shown in FIG. 1, a beam axis of a particle beam immediately after its extraction, that is, a travelling direction of the particle beam is defined as Z11 axis. The extractor 102 is configured such that among bundles of charged particles which circulate in the synchrotron accelerator 100, charged particles in the outer part of a circular track are cut so as to separate from the circular track and are extracted to the outside of the synchrotron accelerator 100.

At a position of the extractor 102, an axis which is perpendicular to Z11 axis and is in a circular track plane is defined as X11 axis. Further, an axis which is perpendicular to Z11 axis and X11 axis is defined as Y11 axis. In the synchrotron accelerator 100, charged particles which are distributed in the direction of X11 axis are extracted to so as to be cut, charged particles which are distributed in the direction of Y11 axis are extracted while maintaining those distribution in the synchrotron accelerator 100. As a result, regarding property of a particle beam which to be extracted, the property of the particle beam in X11 axis is different from the property of the particle beam in Y11 axis direction. A particle beam which is extracted by the above-mentioned extraction method has comparatively small emittance in X11 direction and comparatively large emittance in Y11 direction.

Emittance is an area of phase-space distribution of a particle beam, magnitude of emittance of each direction of X11 and Y11 is not changed while a particle beam travels in the particle beam transportation unit 200 which is composed only of electromagnets. At a gantry incidence position 10 which is a position where the particle beam travels in the particle beam transportation unit 200 and is incident on a gantry, an axis of each direction which is on a particle beam (direction where emittance of each direction is maintained), that is, an axis of each direction at the extractor 102 is defined as X12, Y12 and Z12. Consequently, the particle beam at the gantry incidence position 10 has comparatively small emittance in X12 direction and comparatively large emittance in Y12 direction. A travelling direction of the particle beam is deflected by a gantry-type particle beam irradiation system, an axis of each direction at an irradiation nozzle incidence position 11 where the particle beam enters is incident on the irradiation nozzle 4 (direction where emittance of each direction is maintained) is defined as X13, Y13 and Z13.

Here, an axis of the irradiation nozzle 4 is determined. Now, zero degree, which is reference of rotation angle of the gantry 1 is defined to be an angle as shown in FIG. 1. That is, the state in which a plane where a beam axis of the particle beam is formed by deflecting the particle beam in the gantry is perpendicular to the circular track plane of the synchrotron accelerator 100 is defined to be reference angle zero degree of the gantry 1. When a reference angle of the gantry 1 is defined as the above-mentioned, in the state where the gantry 1 is zero degree, regarding the particle beam which is incident on the irradiation nozzle 4, emittance in X11 direction and emittance in Y11 direction are not combined at an extraction position of the synchrotron accelerator 100, emittance of each direction is separated and maintained. Regarding an axis of the irradiation nozzle 4, a travelling direction of the particle beam is defined as Z2 axis, a direction which coincides with X13 is defined as X2 axis, and a direction coinciding with Y13 is defined as Y2 axis. The X2 axis, the Y2 axis and the Z2 axis are fixed to the irradiation nozzle 4 which rotates together with the rotation of the gantry 1. That is, the X2 axis, the Y2 axis and the Z2 axis are moving axes which rotate together with the rotation of the gantry 1.

Figure 3:
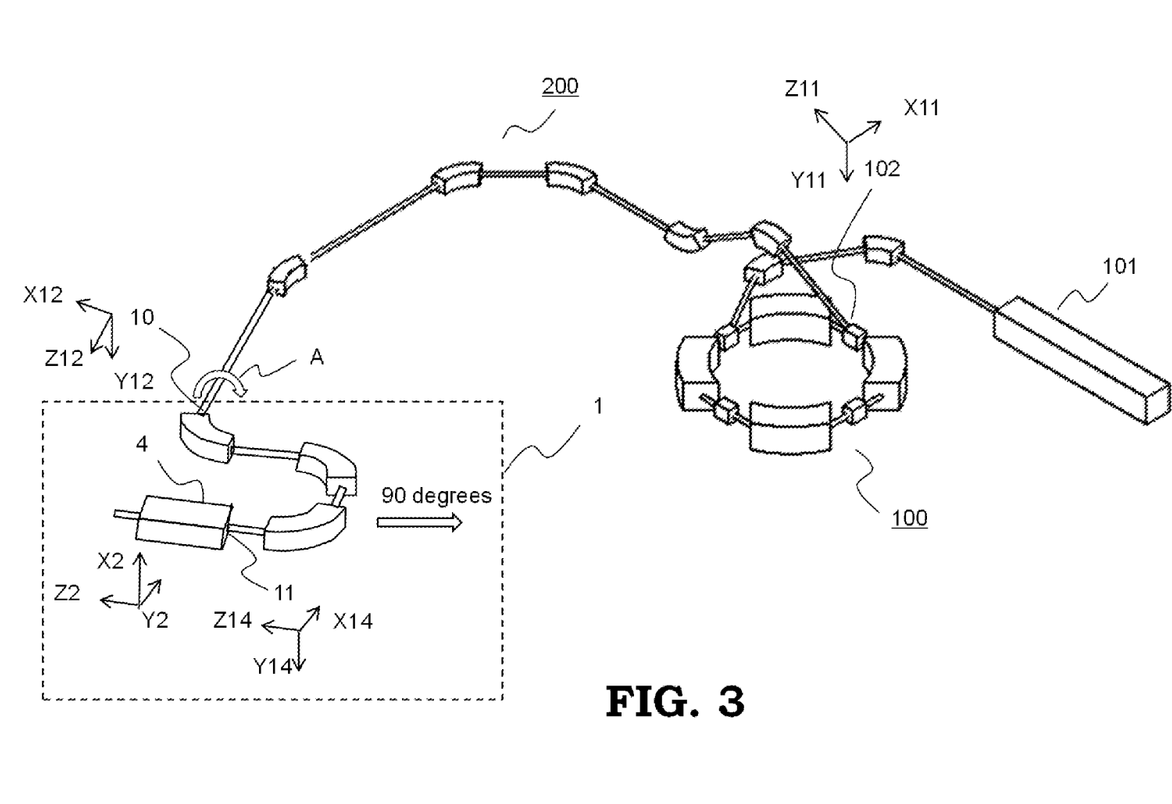
FIG. 3 is another diagram showing an outline of configuration for describing a particle beam irradiation system which is installed in a particle beam therapy system in Embodiment 1 of this invention.

FIG. 3 is a diagram showing an outline of whole of a particle beam irradiation system whose gantry 1 rotates by 90 degrees from the state of reference angle shown in FIG. 1. Even in the state in which the gantry 1 rotates by 90 degrees, in the same way as that of the state of reference angle, emittance in X11 direction and emittance in Y11 direction are not combined at an extraction position of the synchrotron accelerator 100, emittance of each direction is separated and maintained. However, in the state where the gantry 1 rotates by 90 degrees, an axis which corresponds to an axis in each direction which is on a particle beam at an irradiation nozzle emission position 11, that is, an axis of each direction which is on the extractor 102 is X14, Y14 and Z14 shown in FIG. 3.

On the other hand, X2, Y2 and Z2 which are fixed to the irradiation nozzle 4 are fixed to the irradiation nozzle 4 as shown in FIG. 3 and change to the rotated direction. The relationship between X2, Y2 Z2 shown in FIG. 1 and the irradiation nozzle 4, and the relationship between X2, Y2 and Z2 shown in FIG. 3 and the irradiation nozzle 4 are the same. However, the direction of X14 and Y14 which are axes on a particle beam (direction where emittance in each direction is maintained) is turned by 90 degrees from the direction of X13 and Y13 which are axes on a particle beam in the state where the gantry 1 is zero degree which is the reference angle, when the irradiation nozzle 4 is reference.

As described referring FIG. 1 and FIG. 3, by rotating the gantry 1, an axis, which is on a particle beam, rotates in the way that is different from that of the irradiation nozzle 4. When an angle of the gantry 1 is zero degree, X2 axis of the irradiation nozzle 4 is defined as a direction where emittance of a particle beam is small, that is, a direction which coincides with a direction of X13. However, when an angle of the gantry 1 rotates by 90 degrees, a direction where emittance of a particle beam is small, that is, a direction of X14 is a direction which coincides with Y2 axis of the irradiation nozzle 4.

A ridge filter 43 which is installed in the irradiation nozzle 4 rotates together with the irradiation nozzle 4 in accordance with the rotation of the gantry 1. The ridge filter is installed so as for a direction where a ridge 431 of the ridge filter 43 extends to be Y2 direction, for example, as shown in FIG. 12. In this case, when an angle of the gantry 1 is zero degree, the direction where emittance is small, that is, the direction of X13 shown in FIG. 1 coincides with the direction which is perpendicular to a ridge of a ridge filter. On the other hand, in the state where an angle of the gantry 1 is 90 degrees, the direction where emittance is small, that is, the direction of X14 shown in FIG. 3 is the direction where a ridge of a ridge filter extends, that is, the direction of Y2 axis. In this case, the direction which is perpendicular to a ridge of a ridge filter is the direction where emittance is large.

Figure 4:
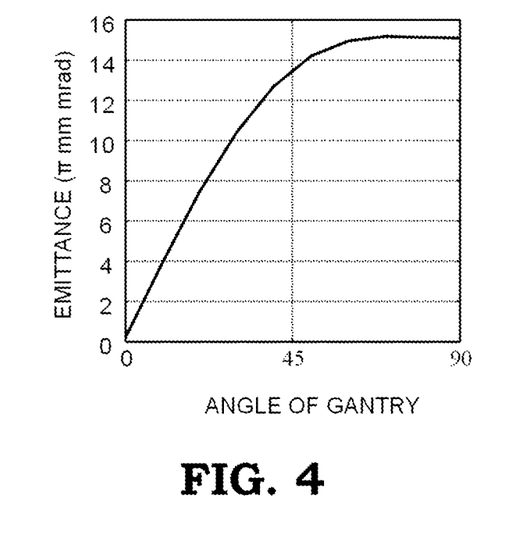
FIG. 4 is a diagram showing change of emittance of a particle beam which is perpendicular to a ridge of a ridge filter with respect to an angle of a gantry of conventional particle beam irradiation system.

FIG. 4 shows change of the emittance in the direction which is perpendicular to a ridge of a ridge filter, when the gantry 1 rotates from zero degree to 90 degrees in a case where the ridge filter 43 is installed for the direction where a ridge of a ridge filter extends is Y2 direction as shown in FIG. 12. In accordance with the rotation of the gantry 1, regarding a particle beam which is incident on the ridge filter 43, emittance of a direction where emittance is small and emittance of a direction where emittance is large, that is, emittance in X12 direction and emittance in Y12 direction at a gantry incidence position 10 is combined, and emittance increases gradually, and when an angle of the gantry 1 is 45 degrees, the above-mentioned combining is maximum. When an angle of the gantry 1 increases to be larger than 45 degrees, the extent of the above-mentioned combining decreases, however, regarding a component of the direction which is perpendicular to the ridge of the ridge filter of the particle beam which is incident on the ridge filter, a component in Y12 direction at the gantry incidence position 10, that is, a component whose emittance is large, increases. Therefore, emittance is continuing at high level. Consequently, emittance in the direction which is perpendicular to the ridge of the ridge filter changes as shown in FIG. 4 together with an angle of the gantry 1. Conventionally, the direction of a ridge of a ridge filter is installed as above mentioned (for example, Patent Document 1).

A particle beam which passed through a ridge filter has an energy distribution which is the same as that of a structure of the ridge filter in the direction which is perpendicular to a ridge of the ridge filter, and in a case where a particle beam whose emittance is small in the above-mentioned direction is incident on a ridge filter, the particle beam irradiates an irradiation target while the particle beam has the above-mentioned energy distribution. Consequently, in the irradiation target, speckled (un-uniform) irradiation distribution is formed.

On the other hand, in a case where a particle beam whose emittance is large in the direction which is perpendicular to a ridge of a ridge filter is incident on a ridge filter, after the particle beam passes through the ridge filter, the particle beam is mixed with other particle beam in accordance with travelling of particle beam. Therefore, a particle beam whose energy width is enlarged by the ridge filter and which has uniform energy distribution is irradiated on an irradiation target so as to form uniform irradiation distribution on the irradiation target. Consequently, in the same way as that of conventional, in a case where a ridge filter is installed so as for the direction which is perpendicular to a ridge of a ridge filter to coincide with the direction where emittance of a particle beam which is incident on a ridge filter is small when an angle of a gantry is zero degree, depending on an angle of the gantry 1, irradiation distribution is speckled (un-uniform).

Even when the gantry rotates, by making a particle beam which has large emittance in the direction which is always perpendicular to a ridge of a ridge filter be incident on a ridge filter, after the particle beam passes through the ridge filter, irradiation distribution of the particle beam in an irradiation target can be made uniform. Alternatively, the irradiation distribution can be suppressed from being speckled. Inventors of this invention found out such that by providing a ridge filter in which the direction of a ridge of the ridge filter is tilted in to X2 axis and Y2 axis which are set on the irradiation nozzle 4, even if an angle of the gantry 1 is any angle, emittance in the direction which is perpendicular to a ridge of the ridge filter is not small. Inventors of this invention found out such that by providing a ridge filter in which the direction of a ridge of a ridge filter is tilted to X2 axis and Y2 axis which are set on the irradiation nozzle 4, even when an angle of the gantry 1 is zero degree, a gantry-type particle beam irradiation system which does not form speckled irradiation distribution in an irradiation target can be obtained. Hereinafter, the configuration of the above-mentioned will be described.

Figure 5:
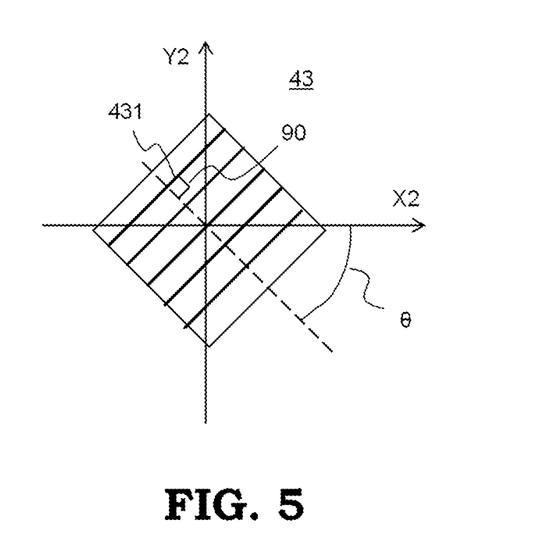
FIG. 5 is a conceptual diagram showing an example of an installation angle of a ridge filter of particle beam irradiation system in Embodiment 1 of this invention.
Figure 6:
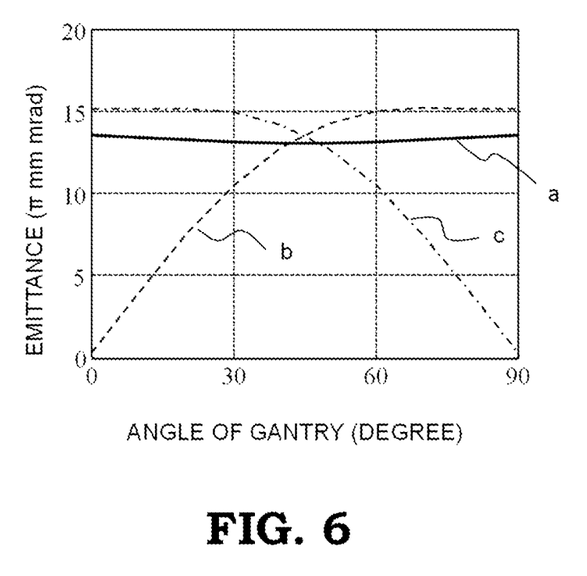
FIG. 6 is a diagram for describing an effect of a particle beam irradiation system in Embodiment 1 of this invention.

FIG. 5 is a conceptual diagram showing an example of a setting angle of a ridge filter of particle beam irradiation system in Embodiment 1 of this invention. An angle θ which is made by X2 axis which is fixed to the irradiation nozzle 4 and the direction which is perpendicular to a ridge 431 of a ridge filter 43 is 45 degrees. FIG. 6 shows how emittance of a particle beam in the direction which is perpendicular to the ridge of the ridge filter changes depending on an angle of the gantry 1 in a case where the ridge filter 43 is installed where the direction which is perpendicular to the ridge 431 of the ridge filter 43 is tilted to X2 axis by 45 degrees. In FIG. 6, a thick solid line a indicates shows change of emittance of a particle beam in the direction which is perpendicular to the ridge of the ridge filter in a case where the direction which is perpendicular to the ridge 431 of the ridge filter 43 is tilted by 45 degrees to X2 axis. As shown in FIG. 6, it is found out such that even when the gantry 1 rotates, emittance of the particle beam in the direction which is perpendicular to the ridge of the ridge filter is almost the same magnitude and hardly changes.

In the same way as that of FIG. 4, a dotted line b in FIG. 6 shows change of emittance of a particle beam in the direction which is perpendicular to a ridge of a ridge filter, in a case where the ridge filter 43 is installed so as for the direction which is perpendicular to the ridge 431 of the ridge filter, 43 is made to be the direction which coincides with X2 axis, that is, an angle θ shown in FIG. 5 is made to be zero degree. Further, a dashed-dotted line c shows change of emittance of a particle beam which is perpendicular to a ridge of a ridge filter in a case where the ridge filter 43 is installed in the direction in which the direction which is perpendicular to the ridge 431 of the ridge filter 43 coincides with Y2 axis. As can be seen from FIG. 6, depending on a set angle of the ridge filter 43, emittance of a particle beam in the direction which is perpendicular to the ridge of the ridge filter greatly changes.

In a case where change of emittance of a particle beam in the direction which is perpendicular to a ridge of a ridge filter is the state which is indicated by a thick solid line a shown in FIG. 6, even when the gantry 1 rotates, change of irradiation distribution in an irradiation target is small, therefore speckled irradiation distribution is not formed. On the other hand, in a case where change of emittance of a particle beam is the state which is indicated by a dotted line b, when an angle of the gantry 1 is approximately zero degree, irradiation distribution is speckled. Further, in a case where change of emittance of a particle beam is the state which is indicated by a dashed-dottedline c, when an angle of the gantry 1 is approximately 90 degrees, irradiation distribution is speckled.

Figure 7:
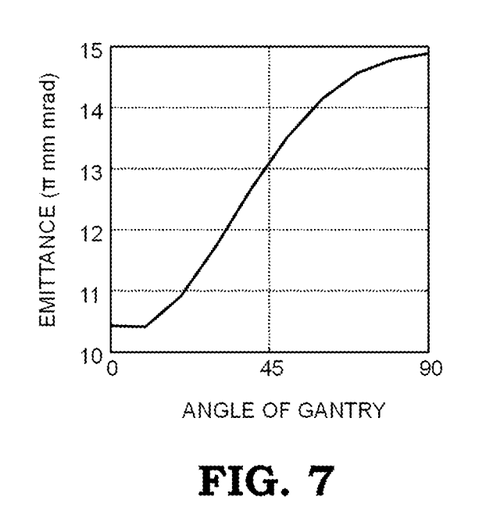
FIG. 7 is another diagram for describing an effect of a particle beam irradiation system in Embodiment 1 of this invention.
Figure 8:
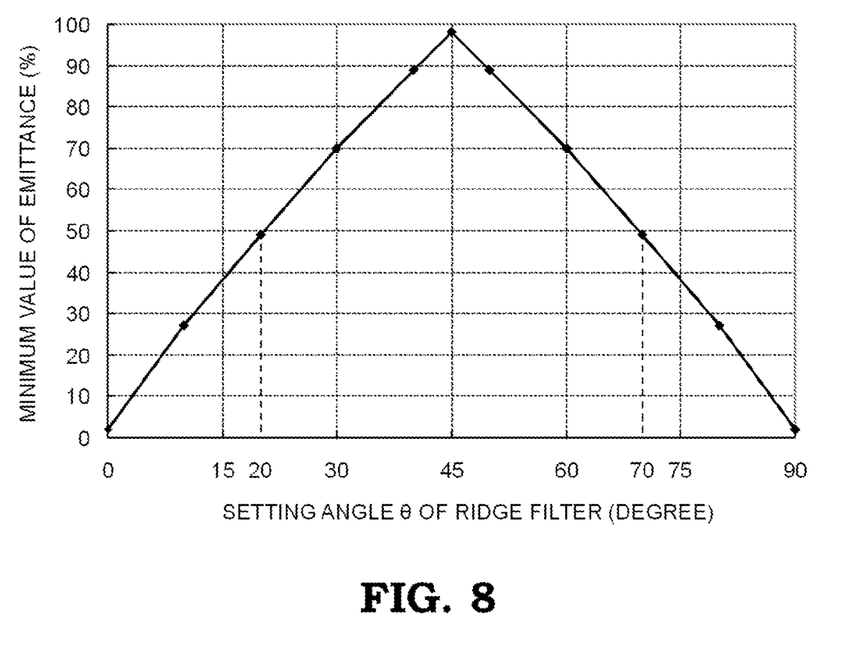
FIG. 8 is another diagram for describing an effect of a particle beam irradiation system in Embodiment 1 of this invention.

FIG. 7 shows change of emittance of a particle beam in the direction which is perpendicular to a ridge of a ridge filter, in a case where the ridge filter 43 is installed so as for an angle θ shown in FIG. 5 to be 30 degrees. In this case, when an angle of the gantry 1 is zero degree, emittance is approximately 10.4 and when an angle of the gantry 1 is 90 degrees, emittance is approximately 14.8. Emittance is 10.4 as minimum, therefore, in this case, irradiation distribution is not speckled. The minimum value 10.4 is 70.3% of the maximum value 14.8. In FIG. 8, a setting angle θ of a ridge filter (θ shown in FIG. 5) is a horizontal axis, in a case where a gantry rotates, the minimum value (the ratio to the maximum value) of emittance of a particle beam in the direction which is perpendicular to a ridge of a ridge filter is a vertical axis. As shown in FIG. 8, even when θ is slightly different from zero degree or from 90 degrees, the minimum value of emittance drastically increases. Especially, when θ is in a range of 20 degrees to 70 degrees, the minimum value of emittance is 50% or more, therefore, irradiation distribution is not speckled. As above mentioned, according to this invention, a ridge filter is installed in which the direction which is perpendicular to a ridge of a ridge filter 43 is tilted to X2 axis. Most preferably, an angle of tilt is 45 degrees; however, it is not necessary for an angle of tilt to be 45 degrees exactly. By setting an angle of tilt to be an range of 20 degrees to 70 degrees, great result can be obtained.

According to this invention, by providing a ridge filter in which the direction which is perpendicular to a ridge of the ridge filter 43 is tilted to X2 axis by a predetermined angle, more preferably 20 degrees to 70 degrees, most preferably 45 degrees, irradiation distribution of a particle beam in an irradiation target is not speckled can be realized, even when a gantry rotates.

Here, X2 axis, that is, an axis which is used as a reference for tilting a ridge filter will be described. A rotation angle of a gantry, by which a particle beam is transported to a ridge filter (or an irradiation nozzle) while emittance of a particle beam in X11 direction which is a circular track plane direction of an accelerator and which is perpendicular to extraction travelling direction of a particle beam at the time of extraction of an accelerator, when a gantry rotates, and emittance in Y11 direction which is perpendicular to X11 direction is not combined and separated and emittance of each direction is maintained is a reference angle. When an angle of the gantry is the reference angle and the direction where emittance in X11 direction is maintained is the direction of an axis (X2) which is used as a reference for tilting a ridge filter. According to this invention, the direction which is perpendicular to a ridge of a ridge filter is tilted to the direction of the axis (X2) which is used as a reference.

Further, in the above description, a reference angle of a gantry is described as zero degree. However, an angle of a gantry, by which a particle beam is transported to a ridge filter while emittance in X11 direction and emittance in Y11 direction is not combined and separated, and emittance in each direction is maintained, is not only zero degree, as shown in FIG. 3, but also 90 degrees, 180 degrees, or 270 degrees, that is, the angle which satisfies the above mentioned condition appears every 90 degrees. Consequently, it is not necessary for a reference angle to be zero angle; a reference angle may be 90 degrees, 180 degrees or 270 degrees.

When the gantry 1 has the configuration as shown in FIG. 1 in which a plane which is formed by a center line of a particle beam which is deflected in the gantry is a flat surface, this invention will be described as following. At an angle of a gantry by which a flat surface which is formed by a center line is perpendicular to a circular track plane of an accelerator, the direction (X13) where emittance in X11 direction at a position of a ridge filter is maintained is a reference axis, a ridge filter is installed in which the direction which is perpendicular to a ridge of the ridge filter is tilted to the direction of the reference axis.

Further, in a case where a gantry is so-called corkscrew type gantry as disclosed in Patent Document 3, a plane which is formed by a center line of a particle beam in a gantry is not a flat surface, however, by rotating the gantry, emittance of a particle beam in X11 direction which is a circular track plane direction of an accelerator and which is perpendicular to extraction travelling direction at the time extraction of an accelerator and emittance in Y direction which is perpendicular to X11 direction is separated, and an angle of the gantry, by which a particle beam is transported to a ridge filter (or an irradiation nozzle) while emittance of each direction is maintained, exists. This rotation angle of the gantry is a reference angle, and the direction where emittance in X11 direction is maintained at this time is the direction of an axis which is used as a reference for tilting the ridge filter. The ridge filter may be installed by tilting the direction which is perpendicular to a ridge of the ridge filter to the direction of the reference axis.

EMBODIMENT 2

Figure 9:
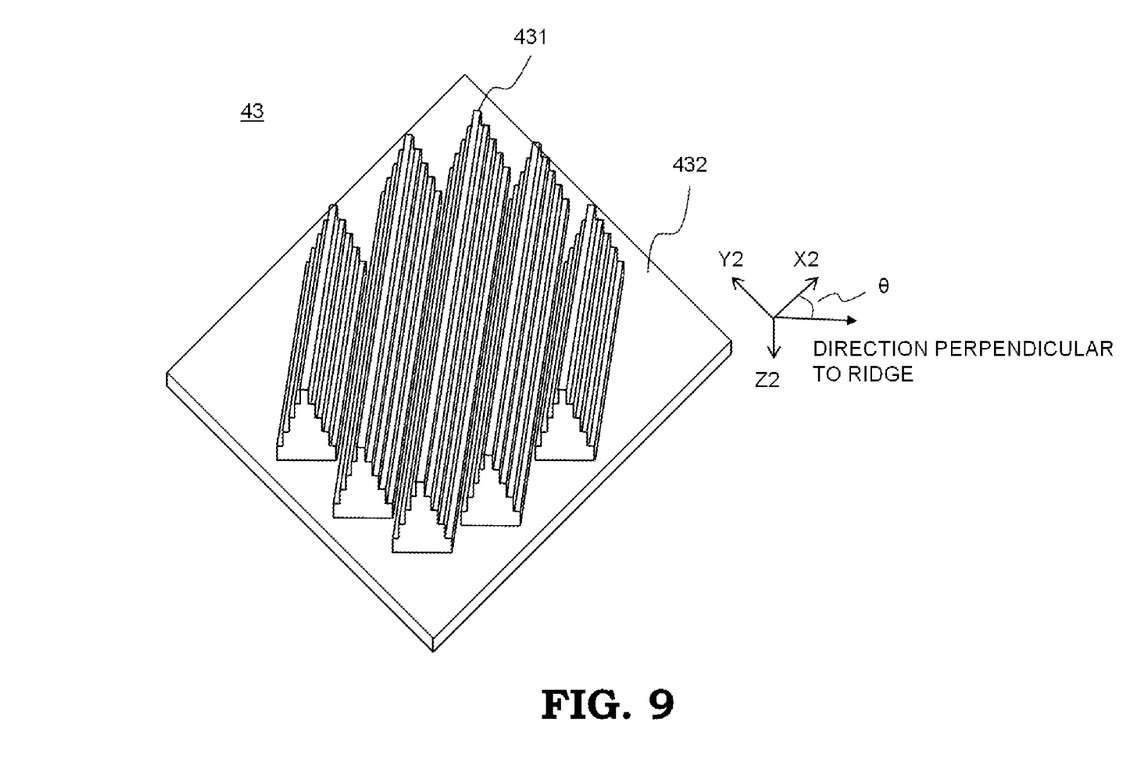
FIG. 9 is an oblique view showing a ridge filter of a particle beam irradiation system in Embodiment 2 of this invention.

FIG. 9 is an oblique view showing a ridge filter 43 of a particle beam irradiation system in Embodiment 2 of this invention. A base 432 of a ridge filter has a rectangular shape, and the ridge filter is attached so as for one side of the rectangular shape to be the direction which is direction of X2 as a reference direction axis of an irradiation nozzle. The ridge filter is installed so as for the direction which is perpendicular to a ridge of a ridge filter to tilt to form an angel θ with one side of a rectangular shape of the base 432 of the ridge filter. By arranging the direction of a ridge of the ridge filter in the above mentioned, by attaching the base 432 of the ridge filter to an irradiation nozzle 4 which is the same as that of conventional type in the same way as that of conventional, the direction which is perpendicular to a ridge of the ridge filter can be attached so as for the direction which is perpendicular to a ridge of the ridge filter to tilt to X2 axis. Consequently, a particle beam irradiation system according to this invention can be obtained easily without modifying an irradiation nozzle of conventional irradiation system.

Figure 10:
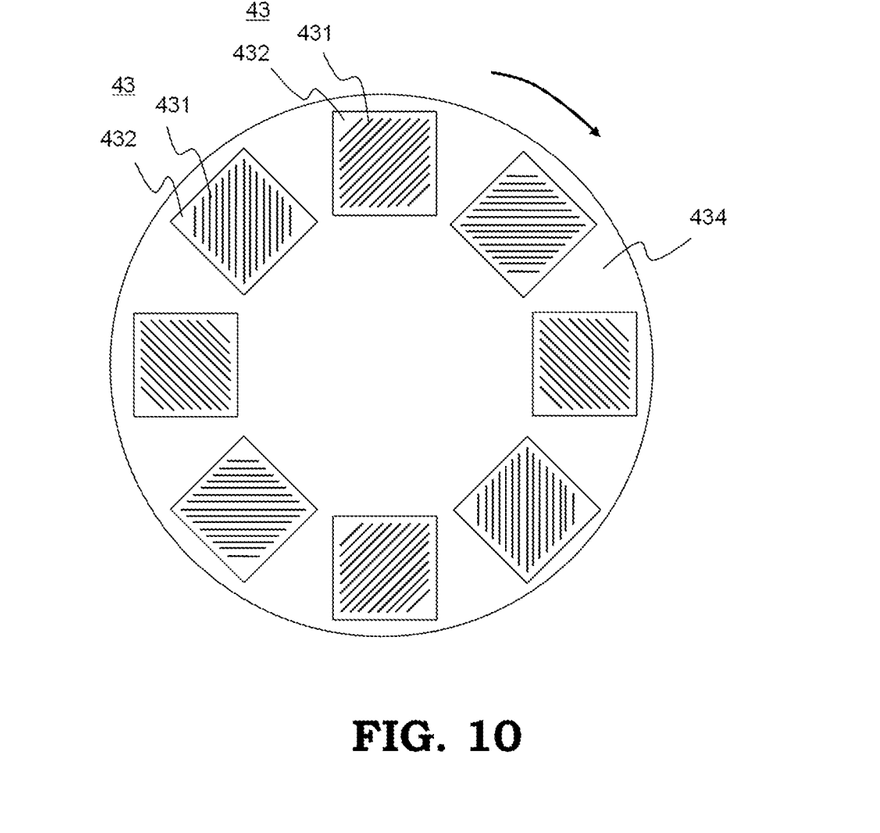
FIG. 10 is a plan showing a rotary fitting table on which a ridge filter of a particle beam irradiation system in Embodiment 2 of this invention is installed.
Figure 11:
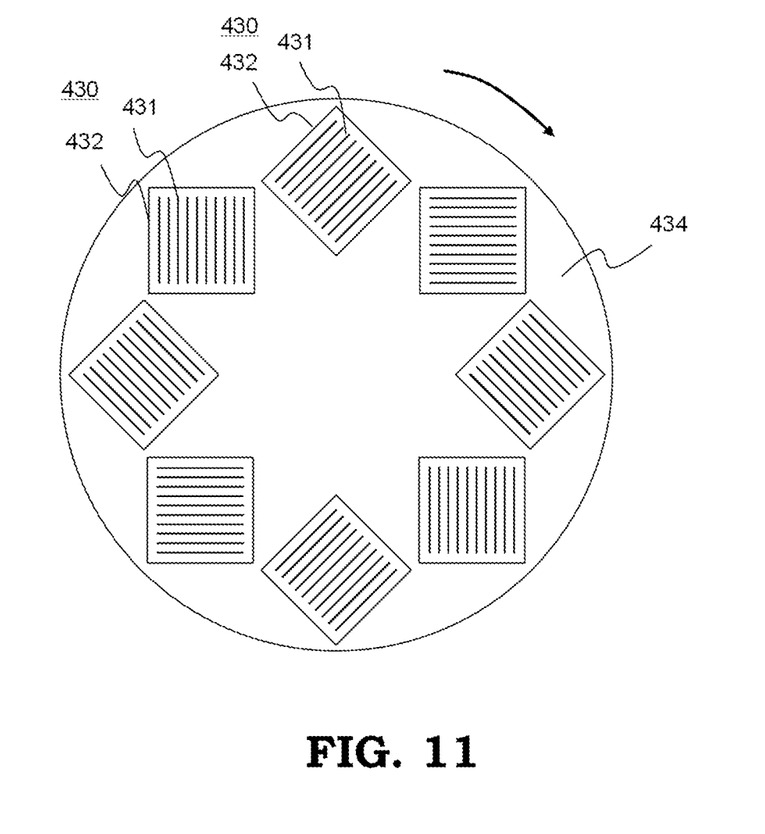
FIG. 11 is a plan showing another rotary fitting table on which a ridge filter of a particle beam irradiation system in Embodiment 2 of this invention is installed.

As shown in FIG. 10, a particle beam irradiation system is configured such that plural kinds of ridge filters having different properties are attached to a plurality of holders which are installed at a rotary fitting table 434 which rotates, depending on a patient as an irradiation target, appropriate ridge filter is selected by rotating the rotary fitting table 434. In this time, as shown in FIG. 9, when a ridge filter is arranged in which the direction which is perpendicular to a ridge of a ridge filter is tilted so as to form an angle θ (in FIG. 9, θ=45 degrees) with one side of a rectangular shape of the base of the ridge filter 432, by attaching to a holder which is same as that of a conventional rotary fitting table 434, a particle beam irradiation system according to this invention can be obtained. On the other hand, in a case where a particle beam irradiation system according to this invention is obtained by attaching a ridge filter 43 shown in FIG. 12 in which the direction which is perpendicular to a ridge 431 of a ridge filter to the rotary fitting table 434, as shown in FIG. 11, it is necessary to tilt and install a holder to be installed on the rotary fitting table 434. In the above-mentioned installation, utilization efficiency on the rotary fitting table 434 is poor, and installation accuracy may be decreased.

EMBODIMENT 1 and EMBODIMENT 2 were described using a synchrotron accelerator 100 as an example of an accelerator, however, in other circular accelerators such as a cyclotron accelerator, emittance of a particle beam which is extracted is directional. That is, in the same way as that of a synchrotron accelerator, emittance of a particle beam in the direction which is perpendicular to extraction travelling direction of a particle beam and in the direction of a circular track plane of an accelerator is small, and emittance in the direction which is perpendicular to that is large. Consequently, according to this invention, by applying not only to a particle beam which is extracted from a synchrotron accelerator but also to a particle beam which is extracted from a circular accelerator, effect which was described in EMBODIMENT 1 and EMBODIMENT 2 using a synchrotron accelerator as an example can be achieved.

REMARKS

1: gantry
4: irradiation nozzle
10: gantry incident position of a particle beam
11: irradiation nozzle incident position of a particle beam
20: patient
30: treatment table
43: ridge filter
100: synchrotron accelerator (circular accelerator)
102: extractor
200: particle beam transportation unit
431: ridge of a ridge filter
432: base of a ridge filter

The invention claimed is:
1. A gantry type particle beam irradiation system which comprises a gantry and is configured such that a particle beam is extracted from a circular accelerator, in a case where a direction in a circular track plane of the circular accelerator is defined as X direction in a plane which is perpendicular to a travelling direction of the particle beam at an extraction position of the circular accelerator, and the direction which is perpendicular to X direction in a plane which is perpendicular to the travelling direction of the particle beam is defined as Y direction, the particle beam has small emittance in X direction and large emittance in Y direction, and the particle beam which is transported by a particle beam transportation unit is irradiated from an irradiation nozzle installed in the gantry to an irradiation target, wherein the irradiation nozzle has a ridge filter, an angle of the gantry, with which the particle beam is transported so as for emittance in X direction and emittance in Y direction at the extraction position of the circular accelerator to be separated and to maintain each emittance at a position where the particle beam is incident on the irradiation nozzle, is defined as a reference angle, in the state where the gantry is the reference angle the ridge filter is installed so as for the direction in which emittance in X direction is maintained is tilted to the direction which is perpendicular to a ridge of the ridge filter by a predetermined angle.

2. The particle beam irradiation system according to claim 1, wherein the predetermined angle is in a range of 20 degrees to 70 degrees.

3. The particle beam irradiation system according to claim 1, wherein the predetermined angle is 45 degrees.

4. The particle beam irradiation system according to claim 1, wherein the ridge filter has a rectangular base, and a direction which is perpendicular to a ridge of the ridge filter is tilted to a direction to which one side of the base extends by a predetermined angle.

5. The particle beam irradiation system according to claim 1, wherein the gantry has the configuration in which a plane which is formed by a center line of the particle beam which is deflected in the gantry is a flat plane, at an angle of the gantry in which the flat plane is perpendicular to the circular track plane of the circular accelerator, a direction in which emittance in the X direction of the particle beam in the irradiation nozzle is maintained is defined as a reference axis and the ridge filter is installed by tilting a direction which is perpendicular to a ridge of the ridge filter to a direction of the reference axis.

6. A particle beam therapy system comprising a circular accelerator, a particle beam transportation unit for transporting a particle beam which is extracted from the circular accelerator, a treatment table for laying a patient and a gantry-type particle beam irradiation system according to claim 1.

* * * * *